United States Patent
Sato et al.

(10) Patent No.: US 10,293,004 B2
(45) Date of Patent: May 21, 2019

(54) BUTYRATE-PRODUCING BACTERIUM AND USE THEREOF

(71) Applicant: KABUSHIKI KAISHA YAKULT HONSHA, Minato-ku (JP)

(72) Inventors: Tadashi Sato, Minato-ku (JP); Shiro Kusuhara, Minato-ku (JP); Wakae Yokoi, Minato-ku (JP); Masahiko Ito, Minato-ku (JP); Kouji Miyazaki, Minato-ku (JP); Akira Kushiro, Minato-ku (JP)

(73) Assignee: KABUSHIKI KAISHA YAKULT HONSHA, Minato-ku (JP)

( * ) Notice: Subject to any disclaimer, the term of this patent is extended or adjusted under 35 U.S.C. 154(b) by 63 days.

(21) Appl. No.: 15/129,849

(22) PCT Filed: Mar. 27, 2015

(86) PCT No.: PCT/JP2015/059670
§ 371 (c)(1),
(2) Date: Sep. 28, 2016

(87) PCT Pub. No.: WO2015/147277
PCT Pub. Date: Oct. 1, 2015

(65) Prior Publication Data
US 2017/0246220 A1    Aug. 31, 2017

(30) Foreign Application Priority Data

Mar. 28, 2014 (JP) .................................. 2014-067726

(51) Int. Cl.
| | | |
|---|---|---|
| *A61K 45/00* | (2006.01) | |
| *A61K 47/00* | (2006.01) | |
| *A01N 63/00* | (2006.01) | |
| *A01N 65/00* | (2009.01) | |
| *A61K 35/74* | (2015.01) | |
| *C12N 1/20* | (2006.01) | |
| *C12P 7/52* | (2006.01) | |
| *C12R 1/01* | (2006.01) | |
| *A23K 10/18* | (2016.01) | |
| *A23K 20/00* | (2016.01) | |
| *A23K 20/105* | (2016.01) | |
| *A23K 20/163* | (2016.01) | |
| *A23L 33/10* | (2016.01) | |
| *A23L 33/135* | (2016.01) | |
| *A23L 33/21* | (2016.01) | |
| *A61K 31/047* | (2006.01) | |
| *A61K 31/7004* | (2006.01) | |
| *A61K 31/7016* | (2006.01) | |
| *A61K 31/702* | (2006.01) | |
| *A61K 31/19* | (2006.01) | |
| *A61K 47/26* | (2006.01) | |
| *C12N 15/09* | (2006.01) | |

(52) U.S. Cl.
CPC .............. *A61K 35/74* (2013.01); *A23K 10/18* (2016.05); *A23K 20/00* (2016.05); *A23K 20/105* (2016.05); *A23K 20/163* (2016.05); *A23L 33/10* (2016.08); *A23L 33/135* (2016.08); *A23L 33/21* (2016.08); *A61K 31/047* (2013.01); *A61K 31/19* (2013.01); *A61K 31/702* (2013.01); *A61K 31/7004* (2013.01); *A61K 31/7016* (2013.01); *A61K 47/26* (2013.01); *C12N 1/20* (2013.01); *C12P 7/52* (2013.01); *C12R 1/01* (2013.01); *A23V 2002/00* (2013.01); *C12N 15/09* (2013.01)

(58) Field of Classification Search
CPC ......... A61K 39/39; A61K 35/74; A61K 35/12
See application file for complete search history.

(56) References Cited

U.S. PATENT DOCUMENTS

2009/0280098 A1    11/2009    Tabata et al.

FOREIGN PATENT DOCUMENTS

| JP | 10-84909 A | 4/1998 |
| JP | 2009-84215 A | 4/2009 |
| WO | 2007/114378 A1 | 10/2007 |

OTHER PUBLICATIONS

H. M. Hamer, et al.. "Review article: the role of butyrate on colonic function," Alimentary Pharmacology & Therapeutics, 2008, vol. 27, pp. 104-119.

Claude C. Roy, et al., "Short-Chain Fatty Acids: Ready for Prime Time?" Nutrition in Clinical Practice, 2006, vol. 21, No. 4, 17 pages.

Jun Zhou, et al., "Peptide YY and Proglucagon mRNA Expression Patterns and Regulation in the Gut," Obesity, Apr. 2006, vol. 14, No. 4, pp. 683-689.

Zhanguo Gao, et al., "Butyrate Improves Insulin Sensitivity and Increases Energy Expenditure in Mice," Diabetes, Jul. 2009, vol. 58, pp. 1509-1517.

Emma Allen-Vercoe, et al., "*Anaerostipes hadrus* comb. nov., a dominant species within the human colonic microbiota; reclassification of Eubacterium hadrum Moore et al. 1976," Anaerobe, 2012, vol. 18, No. 5, pp. 523-529.

(Continued)

*Primary Examiner* — Gary B Nickol
*Assistant Examiner* — Lakia J Jackson-Tongue
(74) *Attorney, Agent, or Firm* — Oblon, McClelland, Maier & Neustadt, L.L.P.

(57) ABSTRACT

A butyrate-producing bacterium belonging to *Anaerostipes hadrus* is provided. The amount of butyrate produced is at least 1.5 times that of *Anaerostipes hadrus* YIT 10092$^T$ (DSM 3319$^T$) and is measured by thawing a frozen stock solution of the bacterial strain (a 10% (w/v) skim milk-2% sodium glutamate solution with suspended bacterial cells) (cell count: 2.0 to 5.5×10$^{10}$ cells/mL), inoculating the solution at 1% to 4 mL of a PY liquid medium supplemented with 33 mM sodium acetate and 0.5 (w/v) % glucose (PYGA medium), followed by anaerobic culture at 37° C. for 24 hours, then inoculating the culture solution at 1% to a PYGA medium, followed by anaerobic culture at 37° C. for 24 hours, then inoculating the culture solution at 1% to a PY medium containing 33 mM sodium acetate and 0.5 (w/v) % L-sorbose, followed by anaerobic culture at 37° C. for 24 hours, and then measuring the butyrate concentration.

4 Claims, 8 Drawing Sheets

Specification includes a Sequence Listing.

(56) References Cited

OTHER PUBLICATIONS

Sylvia H. Duncan, et al., "Lactate-Utilizing Bacteria, Isolated from Human Feces, That Produce Butyrate as a Major Fermentation Product," Applied and Environmental Microbiology, Oct. 2004, vol. 70, No. 10, pp. 5810-5817.

Petra Louis, et al., "Restricted Distribution of the Butyrate Kinase Pathway among Butyrate-Producing Bacteria from the Human Colon," Journal of Bacteriology, Apr. 2004, vol. 186, No. 7, 9 pages.

Thi Phuong Nam BUI, et al., "*Anaerostipes rhamnosivorans* sp. nov., a human intestinal, butyrate-forming bacterium," International Journal of Systematic and Evolutionary Microbiology, 2014, vol. 64, No. 3, 12 pages.

Andreas Schmertz, et al., "*Anaerostipes caccae* gen. nov., sp. nov., a New Saccharolytic, Acetate-utilising, Butyrate-producing Bacterium from Human Faeces," Systematic and Applied Microbiology, 2002, vol. 25, No. 1, pp. 46-51.

Tadashi Sato, et al., "Investigation of Butyrate-producing ability in vivo of human intestinal bacteria converting lactate into butyrate," Japanese Journal of Bacteriology, Feb. 25, 2006, vol. 61, No. 1 (With partial English translation), 3 pages.

International Search Report dated Jun. 30, 2015 in PCT/JP2015/059670 filed Mar. 27, 2015.

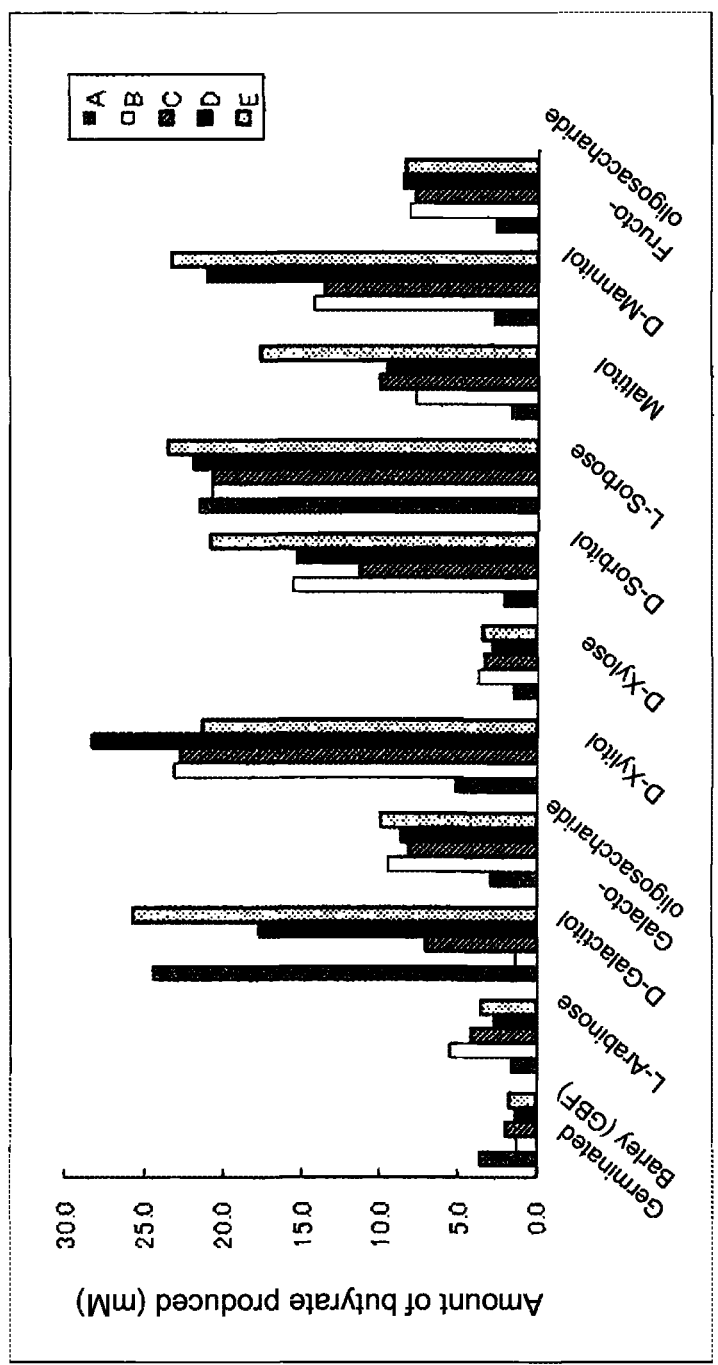
[Figure 1]

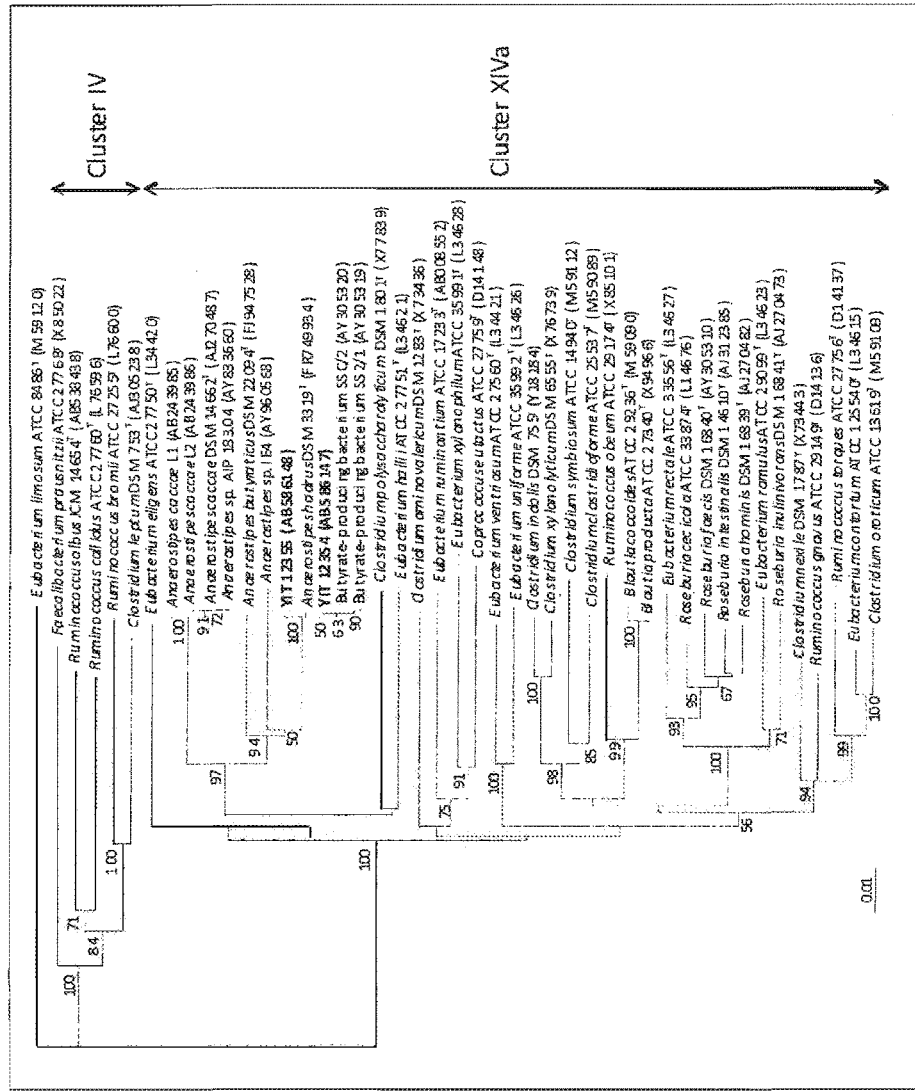
[Figure 2]

[Figure 3]
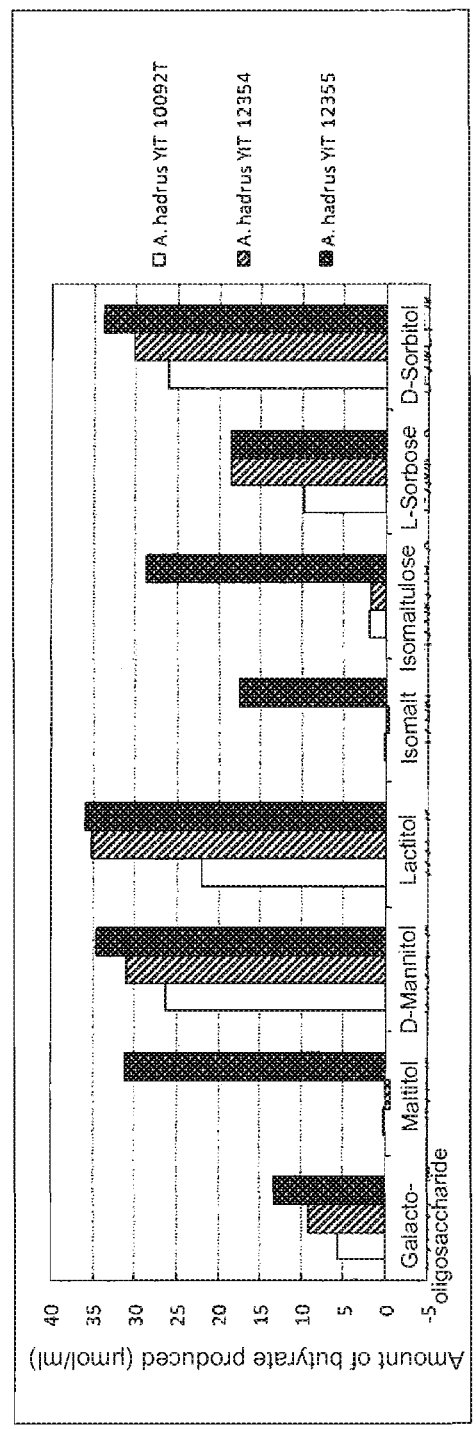

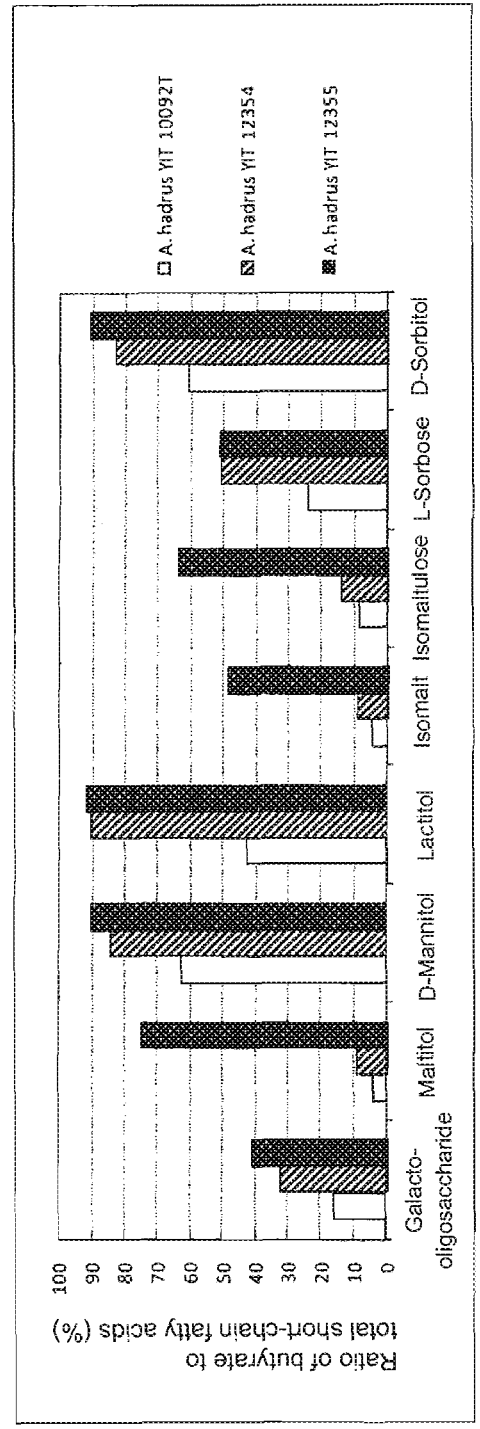
[Figure 4]

[Figure 5]
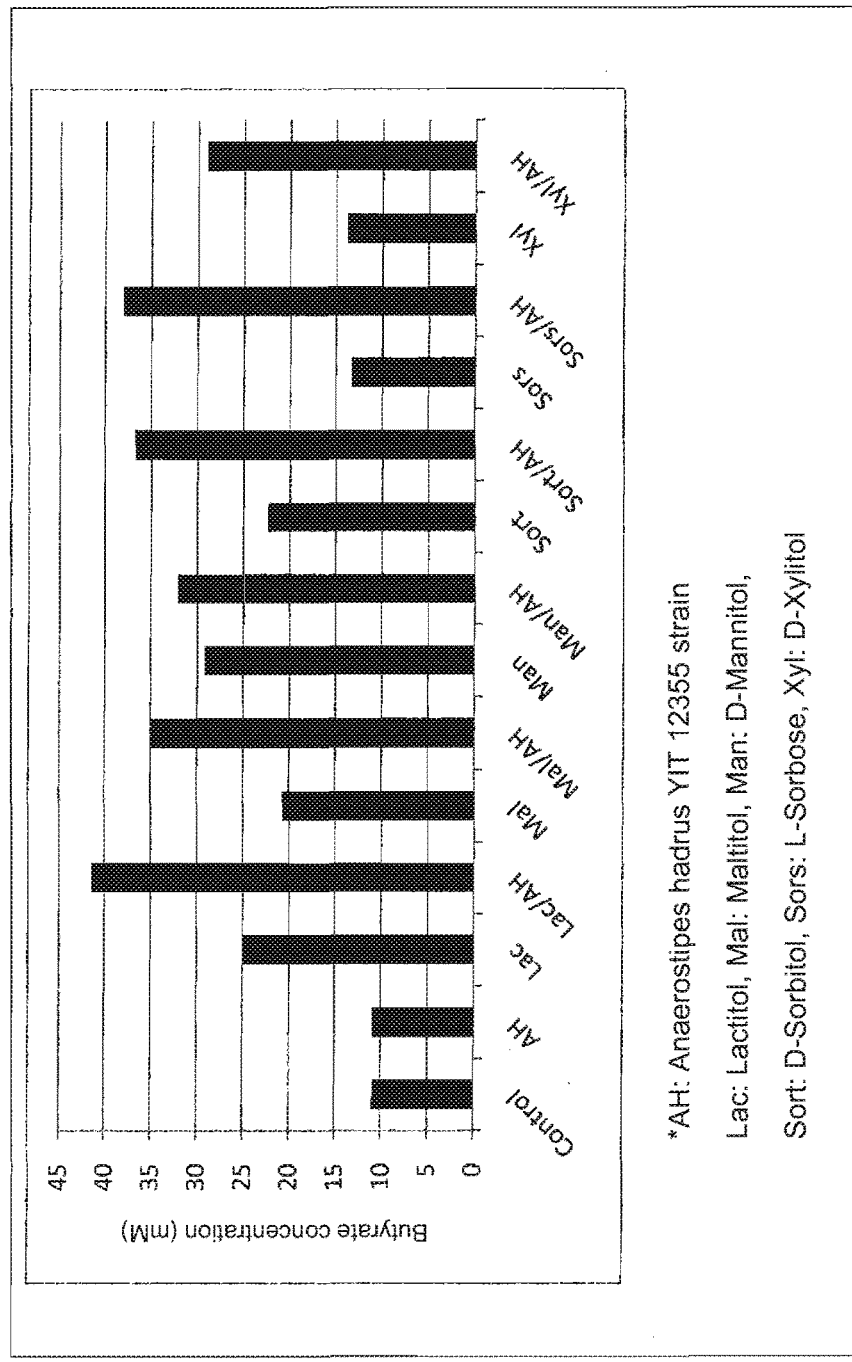

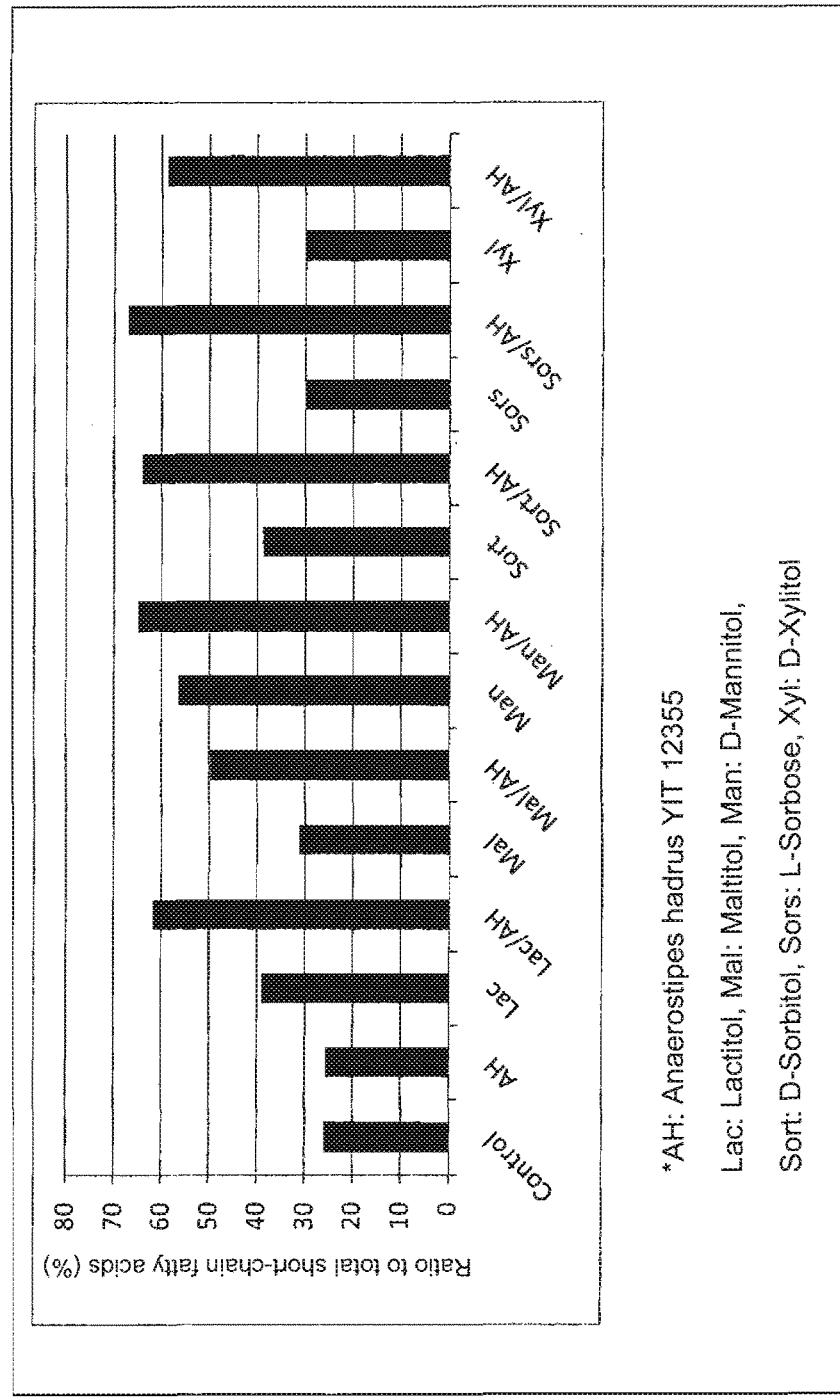
[Figure 6]

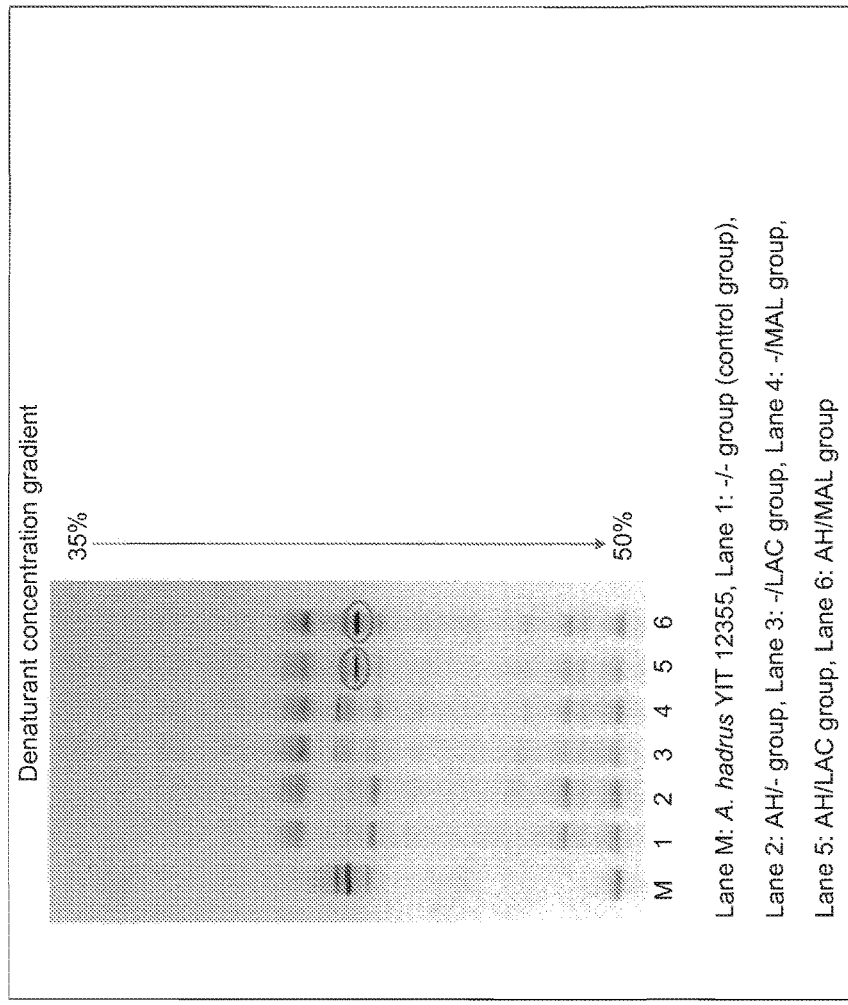

[Figure 8]
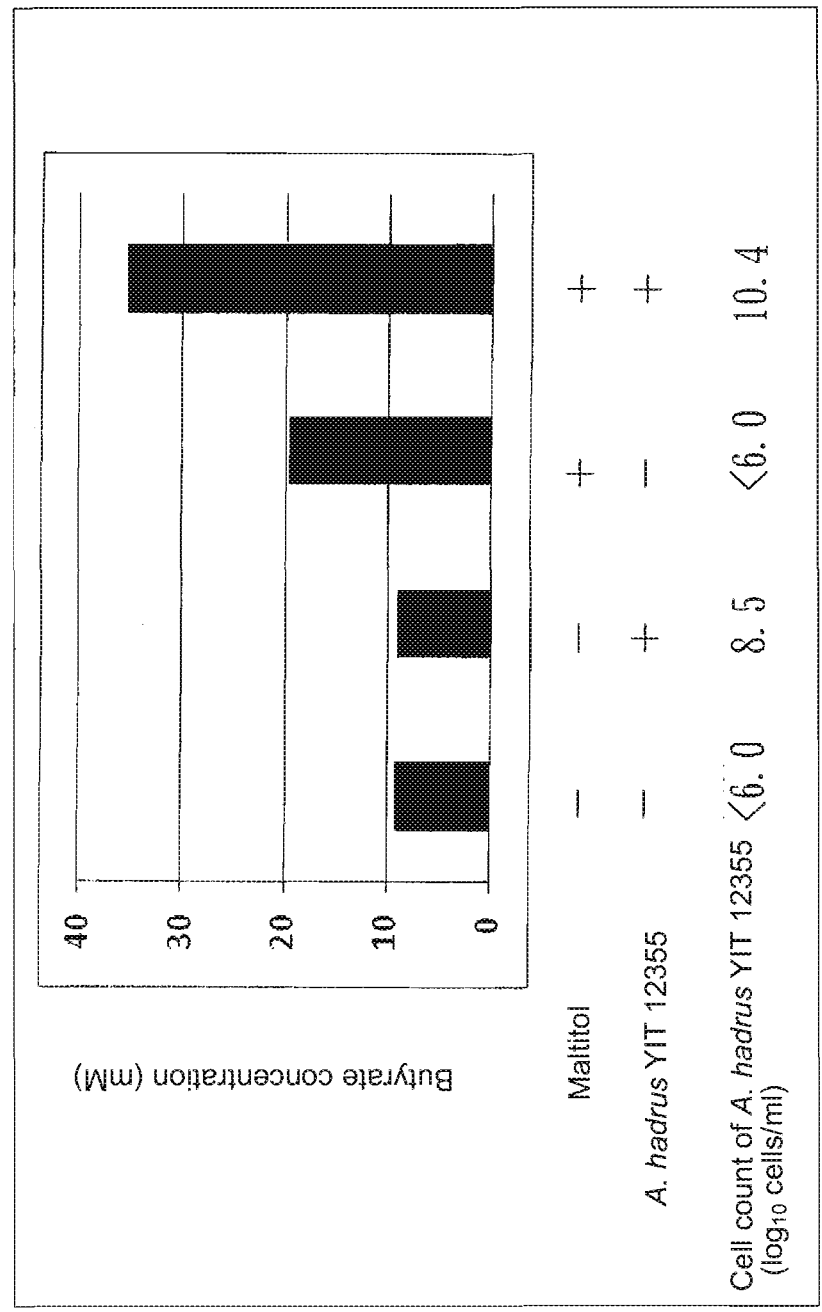

BUTYRATE-PRODUCING BACTERIUM AND USE THEREOF

FIELD OF THE INVENTION

The present invention relates to a novel butyrate-producing bacterium and a composition for food or drink products, medicaments or feed comprising the same.

BACKGROUND OF THE INVENTION

Short-chain fatty acids such as acetic acid, propionic acid and butyric acid are produced by the fermentation of indigestible carbohydrates derived mainly from food by intestinal bacteria in the lower gastrointestinal tract. The short-chain fatty acids are not only utilized as a primary energy source for large intestine mucous membrane epithelial cells but exhibit many physiological effects. Particularly, butyric acid is considered to exhibit diverse physiological activities such as an epithelial cell growth-promoting effect, an anti-inflammatory effect and a bowel motility-enhancing effect (Non Patent Literatures 1 and 2). Also, it has been suggested that butyric acid is important for the prevention of colorectal cancer or ulcerative colitis (Patent Literature 1). In recent years, butyric acid has been reported to promote the secretion of gastrointestinal hormones from the lower gastrointestinal tract (Non Patent Literature 3) and to increase energy consumption in peripheral tissues through oral administration to suppress obesity while improving insulin resistance (Non Patent Literature 4), for example.

Certain bacteria of the genus *Lactobacillus* and the genus *Bifidobacterium* are known as agents for promoting a rise in intestinal butyrate concentration (Patent Literature 1). Also, bacteria belonging to *Anaerostipes*, particularly, *Anaerostipes hadrus* (*Eubacterium hadrum*) (hereinafter, referred to as *A. hadrus*) DSM 3319$^T$, Butyrate-producing bacterium SSC/2, Butyrate-producing bacterium SS2/1 and the like are known as bacteria producing butyrate (Non Patent Literatures 5, 6 and 7).

CITATION LIST

Patent Literature

Patent Literature 1: JP-A-10-084909

Non Patent Literature

Non Patent Literature 1: Hamwe HM et al., Review article: the role of butyrate on colonic function. Aliment Pharmacol Ther. 27: 104-119 (2008)
Non Patent Literature 2: Roy CC et al., Short-chain fatty acids: ready for prime time? Nutr Clin Pract. 21: 351-366 (2006)
Non Patent Literature 3: Zhou J et al., Peptide YY and proglucagon mRNA expression patterns and regulation in the gut. Obesity. 14: 683-689 (2006)
Non Patent Literature 4: Gao Z et al., Butyrate improves insulin sensitivity and increases energy expenditure in mice. Diabetes. 58: 1509-1517 (2009)
Non Patent Literature 5: Allen-Vercoe et al., Anaerobe 18 (2012) 523-529
Non Patent Literature 6: Applied and Environmental Microbilogy (2004) p. 5810-5817
Non Patent Literature 7: J. Bacteriology 2004, 186 (7): 2099-2106

SUMMARY OF THE INVENTION

Problems to be Solved by the Invention

However, the amounts of butyrate produced by the bacterial strains described above are not sufficient. Thus, there has been a demand for a bacterium having the ability to produce butyrate more highly.

Thus, an object of the present invention is to provide a novel butyrate-producing bacterium having the ability to highly produce butyrate, and a composition for food or drink products, medicaments or feed comprising the bacterium.

Means for Solving the Problems

Accordingly, the present inventors have found that the amount of butyrate produced is increased by adding an indigestible saccharide to a sample library possessed by the applicant, followed by culture. Further, as a result of culturing and screening the library using L-sorbose or D-xylitol as the indigestible saccharide, they have found a novel butyrate-producing bacterium having the ability to produce butyrate at least 1.5 times that of an *A. hadrus* type strain YIT 10092$^T$ (DSM 3319$^T$) when using L-sorbose as a substrate. They have also found that the administration of a composition comprising the butyrate-producing bacterium and an indigestible saccharide to animals including humans increases the butyrate-producing bacterium in the intestine and enhances the production of butyrate in the intestine. On the basis of these findings, the present invention has been completed.

Specifically, the present invention provides the following [1] to [5].

[1] A butyrate-producing bacterium belonging to *Anaerostipes hadrus* (*Eubacterium hadrum*), wherein the amount of butyrate produced which is measured by thawing a frozen stock solution of the bacterial strain (a 10% (w/v) skim milk-2% sodium glutamate solution in which bacterial cells are suspended) (cell count: 2.0 to 5.5×10$^{10}$ cells/mL), inoculating the solution at 1% to 4 mL of a PY liquid medium supplemented with 33 mM sodium acetate and 0.5 (w/v) % glucose (PYGA medium), followed by anaerobic culture at 37° C. for 24 hours, then inoculating the culture solution at 1% to a PYGA medium, followed by anaerobic culture at 37° C. for 24 hours, then inoculating the culture solution at 1% to a PY medium containing 33 mM sodium acetate and 0.5 (w/v) % L-sorbose, followed by anaerobic culture at 37° C. for 24 hours, and then measuring the butyrate concentration in the culture solution is at least 1.5 times that of *Anaerostipes hadrus* (*Eubacterium hadrum*) YIT 10092$^T$ (DSM 3319$^T$), which is a type strain of *Anaerostipes hadrus* (*Eubacterium hadrum*).

[2] The butyrate-producing bacterium according to [1], wherein the butyrate-producing bacterium is *Anaerostipes hadrus* (*Eubacterium hadrum*) YIT 12354 (NITE BP-01831) or *Anaerostipes hadrus* (*Eubacterium hadrum*) YIT 12355 (NITE BP-01832).

[3] A composition for food or drink products, medicaments or feed comprising an indigestible saccharide and a butyrate-producing bacterium according to [1] or [2].

[4] The composition according to [3], wherein the indigestible saccharide is one or more members selected from the group consisting of isomalt, isomaltulose, D-galactitol, D-xylitol, D-sorbitol, L-sorbose, maltitol, D-mannitol, lactitol and galactooligosaccharide.

[5] A butyrate production-enhancing agent comprising a composition according to [3] or [4].

Effects of the Invention

The administration of the butyrate-producing bacterium of the present invention together with an indigestible saccharide to animals including humans increases the butyrate-producing bacterium in the intestine and consequently enhances butyrate production in the intestine. The increased amount of butyrate in the intestine enhances various physiological effects based on butyrate as mentioned above.

BRIEF DESCRIPTION OF THE DRAWINGS

FIG. 1 shows the amount of butyrate produced when various indigestible saccharides were added to 5 samples (A to E) selected from the library.

FIG. 2 shows results of the phylogenetic analysis of isolates based on the 16S rRNA gene sequences. Two isolates (YIT 12354 and YIT 12355) are indicated in bold type. The phylogenetic tree was prepared by the neighbor joining method, and a number was described in a position with a Bootstrap value of 50% or more (1,000 repetitions). The scale bar represents that base substitution occurred 0.01 times at the locus.

FIG. 3 shows the amount of butyrate produced when a butyrate-producing bacterium was cultured in a medium with an indigestible saccharide as a substrate.

FIG. 4 shows the ratio of butyrate to total short-chain fatty acids when a butyrate-producing bacterium was cultured in a medium with an indigestible saccharide as a substrate.

FIG. 5 shows a butyrate concentration when an indigestible saccharide and *A. hadrus* YIT 12355 were added into mouse feces.

FIG. 6 shows the ratio of butyrate to total short-chain fatty acid when an indigestible saccharide and *A. hadrus* YIT 12355 were added to mouse feces.

FIG. 7 shows the DGGE profile of bacterium-derived 16S rRNA gene in cecal contents after administration of an indigestible saccharide and *A. hadrus* YIT 12355 to a mouse.

FIG. 8 shows the effect of combined use of maltitol and *A. hadrus* YIT 12355 in a mouse feces culture system.

MODES FOR CARRYING OUT THE INVENTION

The butyrate-producing bacterium of the present invention belongs to *A. hadrus* (*Eubacterium hadrum*), and the amount of butyrate produced by the bacterium with L-sorbose as a substrate is at least 1.5 times that of *A. hadrus* (*Eubacterium hadrum*) YIT 10092$^T$, which is a type strain of *A. hadrus* (*Eubacterium hadrum*). The amount of butyrate produced with L-sorbose as a substrate is preferably 1.5 to 2.5 times, more preferably 1.5 to 2.0 times, even more preferably 1.5 to 1.7 times that of YIT 10092$^T$.

Unlike *A. hadrus* YIT 10092$^T$, the butyrate-producing bacterium of the present invention can produce butyrate with D-xylitol as a substrate.

In this context, the amount of butyrate produced with L-sorbose or D-xylitol as a substrate is the amount of butyrate produced by culture in a medium supplemented with only L-sorbose or D-xylitol as a saccharide. The medium composition and the culture conditions may be conditions suitable for the usual culture of butyrate-producing bacteria. For example, the amount of butyrate produced can be measured by thawing a frozen stock solution of the bacterial strain (a 10% (w/v) skim milk-2% sodium glutamate solution in which bacterial cells are suspended) (cell count: 2.0 to 5.5×10$^{10}$ cells/mL), inoculating the solution at 1% to 4 mL of a PY (peptone-yeast extract) liquid medium supplemented with 33 mM sodium acetate and 0.5 (w/v) % glucose (PYGA medium), followed by anaerobic culture at 37° C. for 24 hours, then inoculating the culture solution at 1% to a PYGA medium, followed by anaerobic culture at 37° C. for 24 hours, then inoculating the culture solution at 1% to a PY medium containing 33 mM sodium acetate and 0.5 (w/v) % L-sorbose or D-xylitol, followed by anaerobic culture at 37° C. for 24 hours, and then measuring the butyrate concentration in the culture solution.

For confirming a cell count after the culture, it is preferred to measure turbidity (OD$_{660}$) after the culture in a PYGA medium and/or the culture in a PY medium containing 33 mM sodium acetate and 0.5 (w/v) % L-sorbose or D-xylitol.

The measurement of the butyrate concentration in the culture solution is not particularly limited as long as the method is capable of measuring the butyrate concentration. For example, the butyrate concentration in the culture solution can be measured by ion-exclusion high-performance liquid chromatography (HPLC).

The butyrate-producing bacterium of the present invention has the property of being able to produce butyrate even in a medium containing only acetic acid (or a salt thereof) as a short-chain fatty acid, not a medium containing many types of short-chain fatty acids (e.g., a YCFA medium containing acetic acid, propionic acid, isobutyric acid, isovaleric acid and valeric acid).

Specific examples of the butyrate-producing bacterium of the present invention include *A. hadrus* (*Eubacterium hadrum*) YIT 12354 (NITE BP-01831) (hereinafter, referred to as YIT 12354) and *A. hadrus* (*Eubacterium hadrum*) YIT 12355 (NITE BP-01832) (hereinafter, referred to as YIT 12355).

The butyrate-producing bacterium of the present invention can be isolated from the library or the like, for example, by inoculating a portion of the library, bacteria collected from nature, or the like to a liquid medium supplemented with an indigestible saccharide as only one sugar source, followed by culture, then spreading the culture solution over a plate medium, picking grown colonies, and measuring the ability to produce butyrate. More specifically, a diluted solution of the library, bacteria collected from nature or the like is inoculated to a liquid medium supplemented with an indigestible saccharide as only one sugar source, followed by culture. On the other hand, the diluted solution is inoculated to a liquid medium without the indigestible saccharide, followed by culture. After the culture, a portion of each culture solution is spread over an agar plate medium supplemented with an indigestible saccharide as only one sugar source, and grown colonies are observed. The colonies obtained from the liquid medium supplemented with an indigestible saccharide are compared with the colonies obtained from the liquid medium without the indigestible saccharide to pick those differing in morphology. The picked bacterial strain is anaerobically cultured in a liquid medium which is a PYA liquid medium (a PY medium supplemented with 33 mM sodium acetate) supplemented with an indigestible saccharide such as L-sorbose as only one sugar source. The butyrate concentration in the culture solution can be measured. In this context, the concentration of the indigestible saccharide to be added is preferably 0.1 to 5.0 (w/v) %, more preferably 0.2 to 1.0 (w/v) %, even more preferably 0.4 to 0.6 (w/v) %. The culture is preferably anaerobic culture at 30 to 40° C. for 12 to 48 hours, more preferably anaerobic culture at 37° C. for 24 hours.

The butyrate-producing bacterium of the present invention can utilize a wide range of types of carbohydrates and has the ability to produce butyrate even when cultured using an indigestible saccharide such as L-sorbose or D-xylitol, which is difficult to be utilized by other bacteria, as a substrate. As described in Examples mentioned later, as a result of conducting phylogenetic analysis based on the 16S rRNA gene sequences, the butyrate-producing bacterium of the present invention is classified into *A. hadrus*. As a result of comparing its biochemical properties with those of the type strain *A. hadrus* YIT 10092$^T$, they differed in enzymatic activity and sugar utilization. Therefore, the butyrate-producing bacterium of the present invention has been identified as a novel bacterial strain different from the type strain. YIT 12354 and YIT 12355 were deposited on Mar. 19, 2014 as Accession Nos. NITE BP-01831 and NITE BP-01832, respectively, with International Patent Organism Depositary of the National Institute of Technology and Evaluation (2-5-8 120, Kazusakamatari, Kisarazu-shi, Chiba, 292-0818, Japan).

The butyrate-producing bacterium of the present invention has no problem associated with safety and has the ability to produce butyrate with an indigestible saccharide as a substrate. Thus, a composition comprising the butyrate-producing bacterium of the present invention and an indigestible saccharide is useful as a composition for food or drink products, medicaments or feed. The composition produces butyrate in the intestines of animals including humans and as such, is useful as a butyrate production-enhancing agent. Butyric acid, as mentioned above, is not only utilized as an energy source for large intestine mucous membrane epithelial cells but has an epithelial cell growth-promoting effect, an anti-inflammatory effect and a bowel motility-enhancing effect and further has a preventive or therapeutic effect on colorectal cancer and ulcerative colitis, and an energy metabolism regulatory effect. Therefore, the composition of the present invention is particularly useful as a medicament, a food or drink product or feed having these physiological activities.

Examples of the indigestible saccharide include: monosaccharides and disaccharides such as L-sorbose, D-xylose, isomaltulose, lactulose and D-trehalose; sugar alcohols such as isomalt, D-galactitol, D-xylitol, D-sorbitol, maltitol, D-mannitol, erythritol and lactitol; oligosaccharides such as galactooligosaccharide, fructooligosaccharide, lactosucrose, isomaltooligosaccharide, soybean oligosaccharide, nigerooligosaccharide, gentiooligosaccharide, pectin oligosaccharide and cyclodextrin; germinated barley; inulin; indigestible dextrin; and resistant starch. Among them, one or more members selected from the group consisting of indigestible saccharides utilizable by the butyrate-producing bacterium of the present invention, particularly, isomalt, isomaltulose, D-galactitol, D-xylitol, D-sorbitol, L-sorbose, maltitol, D-mannitol, lactitol and galactooligosaccharide, are preferred.

The composition of the present invention preferably contains $10^4$ cfu to $10^{14}$ cfu of the butyrate-producing bacterium as live cells. The composition of the present invention preferably contains 0.01 (w/v) % to 90 (w/v) %, more preferably 0.05 (w/v) % to 50 (w/v) %, of the indigestible saccharide.

The composition of the present invention can be in a form suitable for each of food or drink product, medicament or feed. In the case of a medicament, the composition of the present invention can be mixed with, for example, a solid or liquid pharmaceutical nontoxic carrier and used in the form of a conventional pharmaceutical preparation. Examples of such a preparation include solid formulations such as tablets, granules, powders and capsules, liquid formulations such as solution, suspensions and emulsions, and freeze-dried preparations. These preparations can be prepared by a conventional means for formulation. Examples of the pharmaceutical nontoxic carrier include glucose, lactose, sucrose, starch, mannitol, dextrin, fatty acid glyceride, polyethylene glycol, hydroxyethyl starch, ethylene glycol, polyoxyethylene sorbitan fatty acid ester, amino acids, gelatin, albumin, water and physiological saline. If necessary, conventional additives such as a stabilizer, a wetting agent, an emulsifier, a binder, a tonicity agent and an excipient can also be appropriately added to the preparations.

In the case of a food or drink product, the composition of the present invention can be in any of solid and liquid forms, for example. In the case of a food or drink product, the composition of the present invention can be contained as it is or contained with various nutrient components. Specifically, the composition of the present invention can be formed as an edible form, i.e., granules, grains, tablets, capsules, pastes, or the like, by use of a conventional means appropriately using additives usable for food or drink products. Examples of the type of the food or drink product include: food products including processed meat products such as ham and sausage, fishery processed food products such as Kamaboko (fish minced and steamed) and Chikuwa (fish sausage), bread, confectionery, butter and powdered milk; and drink products such as water, fruit juice, milk, soft drinks and tea drinks. The same holds true for the feed.

When administered to animals including humans, the composition of the present invention is preferably administered through an oral route from the viewpoint of producing butyrate in the intestine. The dose thereof is preferably $1.0 \times 10^4$ cfu or more, more preferably $1.0 \times 10^8$ cfu to $1.0 \times 10^{12}$ cfu in terms of a viable count as the butyrate-producing bacterium per day.

EXAMPLES

Next, the present invention will be described in detail with reference to Examples.

Example 1

Isolation of Butyrate-producing Bacterium (1) Butyrate Production-promoting Effects of Various Indigestible Saccharides by Culture of Sample Library Five samples (A to E) were selected from the sample library possessed by the applicant and each transferred into a glove box, and 20 g of each sample was transferred to a homogenizer bag PYXON-30 (manufactured by ELMEX) with a filter. Each sample was diluted 10-fold by the addition of an anaerobically substituted 0.1 M sodium phosphate buffer solution (pH 6.8) thereto in 9 times the amount of each sample. Then, the mixture was filtered through the filter, and the residue was removed to prepare a diluted sample solution. 0.5 mL (final saccharide concentration: 0.5 (w/v) %) of a 10 (w/v) % solution of each saccharide, i.e., germinated barley (GBF), L-arabinose, D-galactitol, galactooligosaccharide, D-xylitol, D-xylose, D-sorbitol, L-sorbose, maltitol, D-mannitol or fructooligosaccharide was added to 9.5 mL of the diluted sample solution, followed by anaerobic culture at 37° C. for 24 hours.

The results are shown in FIG. 1. As seen from FIG. 1, the amount of butyrate produced was increased by the addition of each indigestible saccharide to the five samples (A to E) and the subsequent culture. Thus, the library was confirmed to contain a butyrate-producing bacterium.

(2) Isolation of YIT 12354 and YIT 12355

Two of the samples (C and E) were each transferred into a glove box. Each sample was sufficiently homogenized, and then a portion thereof was transferred to a homogenizer bag PYXON-30 (manufactured by ELMEX) with a filter. Each sample was homogenized by the addition of an anaerobically substituted 0.1 M sodium phosphate buffer (pH 6.8) thereto in 9 times the amount of each sample, and the residue was removed. The diluted sample solution was inoculated at 0.5% to a PY liquid medium (Table 1), a PY liquid medium supplemented with 0.5 (w/v) % L-sorbose (PYS), or a PY liquid medium supplemented with 0.5 (w/v) % D-xylitol (PYX), followed by anaerobic culture at 37° C. for 24 hours. After the culture, the culture solution was diluted $10^{6-7}$-fold with anaerobically substituted PBS, and spread over a PY, PYS or PYX agar plate medium, followed by anaerobic culture at 37° C. for 72 hours. Among colonies grown on the PYS or PYX plate medium, colonies differing in morphology from those grown on the PY plate medium were picked and inoculated to a PYS or PYX liquid medium, followed by anaerobic culture at 37° C. for 24 hours. These isolates were screened for strains producing butyrate into the culture solution. As a result, two isolates (YIT 12354 and YIT 12355) were selected.

TABLE 1

PY medium composition (per 1 L)

| | |
|---|---|
| Peptone | 5.0 g |
| Trypticase Peptone | 5.0 g |
| Yeast extract | 10.0 g |
| 0.1% resazurin solution | 1.0 mL |
| Salt solution I*[1] | 40.0 mL |
| Salt solution II*[2] | 20.0 mL |
| 0.05% hemin solution | 10.0 mL |
| 8% sodium carbonate | 50.0 mL |
| L-cysteine hydrochloride monohydrate | 0.5 g |
| 1% vitamin $K_1$ solution in ethanol | 0.1 mL |

Anaerobically substituted with $CO_2$ gas, pH 6.9.
The plate medium was prepared by adding 1.6% agar to the above composition.
Sterilized in an autoclave at 121° C. for 15 minutes
*[1]Salt solution I (per 1 L)

| | |
|---|---|
| Calcium chloride | 0.2 g |
| Magnesium sulfate heptahydrate | 0.048 g |
| Sodium chloride | 1.0 g |
| Potassium dihydrogen phosphate | 1.0 g |
| Sodium bicarbonate | 2.0 g. |

*[2]Salt solution II (per 1 L)

| | |
|---|---|
| Dipotassium hydrogen phosphate | 20.0 g. |

Example 2

Feature of YIT 12354 and YIT 12355-1

(1) Amount of Butyrate Produced
1) Production of Butyrate by Each Bacterial Strain from L-sorbose and D-xylitol A frozen stock solution of each bacterial strain (a 10% (w/v) skim milk-2% sodium glutamate solution in which bacterial cells were suspended) (cell count: 2.0 to 5.5×10^{10} cells/mL) was thawed, and the solution was inoculated at 1% to 4 mL of a PY liquid medium supplemented with 33 mM sodium acetate and 0.5 (w/v) % glucose (PYGA medium), followed by anaerobic culture at 37° C. for 24 hours. After the culture, the culture solution was inoculated at 1% to a fresh PYGA medium, followed by anaerobic culture at 37° C. for 24 hours. After the culture, the turbidity ($OD_{660}$) of the culture solution was measured. Then, the culture solution was inoculated at 1% to a PY medium containing 0.5 (w/v) % L-sorbose or D-xylitol and 33 mM sodium acetate (the medium containing L-sorbose: PYSA, and the medium containing D-xylitol: PYXA), followed by anaerobic culture at 37° C. for 24 hours. Then, the turbidity ($OD_{660}$) was measured.

After the completion of the culture, the organic acid concentration in the culture solution was quantified by ion-exclusion HPLC. In this operation, a culture solution in a PY medium supplemented with sodium acetate but without L-sorbose or D-xylitol (PYA medium) was used as a blank.

TABLE 2

(Turbidity measurement results)

Turbidity ($OD_{660}$) after anaerobic culture at 37° C. for 24 hours in PYGA liquid medium
Turbidity ($OD_{660}$)

| YIT 10092$^T$ | YIT 12354 | YIT 12355 |
|---|---|---|
| 2.80 | 2.76 | 3.55 |

Turbidity ($OD_{660}$) after anaerobic culture at 37° C. for 24 hours of 1% inoculum in PYSA or PYXA Turbidity ($OD_{660}$)

| Medium | YIT 10092$^T$ | YIT 12354 | YIT 12355 |
|---|---|---|---|
| PYSA | 2.56 | 2.26 | 2.39 |
| PYXA | 0.11 | 1.09 | 1.47 |

(HPLC Analysis Conditions)
Eluent: 15 mM perchloric acid-7% acetonitrile
pH adjuster: 15 mM perchloric acid-60 mM tris(hydroxymethyl)aminomethane-7% acetonitrile
Separation column: Organic acid analysis column RSpak KC-811×2 (manufactured by Showa Denko K.K.)
Column temperature: 42° C.
Injected sample volume: 10 μL
Flow rate: 1.0 mL/min
Analysis time: 35 min
Detector: Waters 432 electric conductivity detector
Cell temperature: 45° C.

The amount of butyrate produced was calculated according to (Expression 1).

Amount of butyrate produced=(Amount of butyrate produced by culture for 24 hours in a PYSA or PYXA medium)−(Amount of butyrate produced by culture for 24 hours in a PYA medium)    (Expression 1)

The results are shown in Table 3.

TABLE 3

Amounts of butyrate produced by various bacterial strains from L-sorbose and D-xylitol

| | Amount of butyrate produced (mmol/L) | |
|---|---|---|
| Bacterial strain | L-Sorbose | D-Xylitol |
| A. hadrus YIT 10092$^T$ | 9.7 | −0.1 |
| Isolate YIT 12354 | 14.8 | 31.0 |
| Isolate YIT 12355 | 15.4 | 31.9 |

From Table 3, the amounts of butyrate produced by the two isolates in the presence of L-sorbose both exhibited at least 1.5 times that of the type strain. The type strain was unable to produce butyrate by utilizing D-xylitol, whereas the two isolates produced butyrate when D-xylitol was used as a substrate.

2) Amount of Butyrate Produced by Culture in Medium Supplemented with Acetate or Lactate Each bacterial solution cultured in a PYGA liquid medium under the same conditions as those described in the preceding paragraph 1) was inoculated at 1% to a PYA medium containing 33 mM sodium acetate and further supplemented with 40 mM sodium lactate, followed by anaerobic culture at 37° C. for 24 hours. After the completion of the culture, the organic acid concentration in the culture solution was analyzed by ion-exclusion HPLC. The analysis conditions were the same as those described in the preceding paragraph 1). The amount of butyrate produced was calculated according to (Expression 2).

Amount of butyrate produced=(Amount of butyrate produced by culture for 24 hours in a PYA medium supplemented with 40 mM sodium lactate)−(Amount of butyrate produced by culture for 24 hours in a PYA medium without 40 mM sodium lactate)  (Expression 2)

The results are shown in Table 4.

TABLE 4

| Bacterial strain | Amount of butyrate produced (mmol/L) |
| --- | --- |
| Isolate YIT 12354 | 16.5 |
| Isolate YIT 12355 | 19.9 |

Non Patent Literature 6 states that the amounts of butyrate produced by known butyrate-producing bacteria SS2/1 and SSC/2 when cultured at 37° C. for 24 hours in a YCFA (33 mM acetic acid+9 mM propionic acid+1.2 mM isobutyric acid+1.0 mM isovaleric acid+1.0 mM valeric acid) medium supplemented with 35 mM lactate were 12.98 mM and 13.49 mM, respectively.

The butyrate-producing bacterium of the present invention was found to have the property of being able to produce butyrate even in a medium containing only acetic acid (or a salt thereof) as a short-chain fatty acid, not a medium containing many types of short-chain fatty acids (e.g., a YCFA medium). Also, the amount of butyrate produced was higher than that of SS2/1 and SSC/2.

(2) Results of Phylogenetic Analysis of Isolates Based on 16S rRNA Gene Sequences DNA was extracted by the bead-phenol method from the culture solution of each bacterial strain, and the full length of 16S rDNA was amplified by PCR. Then, almost the full length of the sequence was sequenced. The obtained sequence was subjected to FASTA search using the DNA Data Bank of Japan (DDBJ) and checked against the sequence database of known bacterial species. Further, the sequence of each isolate was phylogenetically analyzed by the neighbor joining (NJ) method using Clustal X, and the phylogenetic tree was prepared using the Tree-View program.

The results are shown in FIG. 2.

As a result of conducting the phylogenetic analysis based on the 16S rRNA gene sequences (approximately 1,450 bp) of YIT 12354 and YIT 12355, both of the strains were positioned in a subcluster of the genus *Anaerostipes* in Clostridial Cluster XIVa and further exhibited 99.7% and 99.8% identity, respectively, to the sequence of *A. hadrus* YIT 10092$^T$, which is a type strain of *A. hadrus* (=*Eubacterium hadrum*). From these results, YIT 12354 and YIT 12355 were both found to be classified into *A. hadrus*.

(3) Comparison of Biochemical Properties of Various Bacterial Strains

Commercially available API-ZYM, Rapid ID32A API, and API KENKI 20A (SYSMEX bioMerieux Co., Ltd.) were used in the testing of biochemical properties of various bacterial strains. The testing method followed the product manuals.

The results are shown in Table 5.

TABLE 5

Comparison of biochemical properties of various bacterial strains

| Test item | *A. hadrus* YIT 10092$^T$ | YIT 12354 | YIT 12355 |
| --- | --- | --- | --- |
| Enzymatic activity | | | |
| Alkaline phosphatase | − | + | + |
| Acid phosphatase | + | + | + |
| Naphthol-AS-B1-phosphohydrolase | + | + | + |
| Esterase (C$_4$) | + | − | + |
| β-Galactosidase | + | + | + |
| β-Galactosidase-6-phosphate | + | − | − |
| α-Glucosidase | − | − | +$^w$ |
| Saccharide fermentability | | | |
| Aesculin | − | − | + |
| L-Arabinose | + | + | + |
| D-Cellobiose | + | − | +$^w$ |
| Glycerol | − | − | +$^w$ |
| Mallose | +$^w$ | +$^w$ | + |
| D-Mannitol | + | + | + |
| Salicin | + | − | + |
| L-Sorbitol | + | + | + |
| D-Raffinose | − | +$^w$ | − |
| L-Rhamnose | − | − | + |
| D-Xylose | + | + | + |

+, positive reaction;
−, negative reaction;
+$^w$, weak reaction

As seen from Table 5, these three bacterial strains were found to exhibit similar properties, which, however, were not the same properties and differ from each other at the strain level. All of the three bacterial strains were gram-positive bacilli.

From these results, YIT 12354 and YIT 12355 were determined as novel bacterial strains and deposited under Accession Nos. NITE BP-01831 and NITE BP-01832, respectively, with International Patent Organism Depositary of the National Institute of Technology and Evaluation.

Example 3

Feature of YIT 12354 and YIT 12355-2 a) Indigestible Saccharide

Galactooligosaccharide (GOS), maltitol, D-mannitol, lactitol, isomalt, isomaltulose, L-sorbose and D-sorbitol were used as indigestible saccharides. These indigestible saccharides used, except for GOS, were reagent grade. GOS used was commercially available Oligomate 55N (Yakult Pharmaceutical Industry Co., Ltd.) from which monosaccharide and lactose fractions (fractions digestible and absorbable by the upper gastrointestinal tract) had been removed using an activated carbon column. Specifically, a saccharide solution diluted with purified water was added to a column packed with activated carbon (manufactured by Wako Pure Chemical Industries, Ltd.) swollen in purified water, and the column was washed with a 2% ethanol solution, followed by the elution of an indigestible fraction with a 50% ethanol solution. The eluate was dried under reduced pressure, and the obtained GOS saccharide solution was used.

b) Bacterial Strain Used

*A. hadrus* YIT 10092$^T$ (DSM 3119$^T$), which is a type strain of *A. hadrus* (a typical human intestinal butyrate-producing bacterium), and two isolates were used.

c) Evaluation of Ability to Produce Butyrate

Each of these bacterial strains was anaerobically cultured at 37° C. for 24 hours in a PYA medium containing 33 mM sodium acetate supplemented with 0.5% D-glucose (PYGA medium). The culture solution was inoculated at 1% to a PYA medium containing 0.5 (w/v) % of each indigestible saccharide (test medium), followed by anaerobic culture at 37° C. for 24 hours. After the completion of the culture, the organic acid concentration in the culture solution was analyzed by ion-exclusion HPLC. The analysis conditions were the same as those described above in Example 2. After the quantification of the organic acid concentration, the amount of butyrate produced from each indigestible saccharide and the ratio of butyrate to total short-chain fatty acids were calculated according to the following expressions.

(Amount of butyrate produced)=(Amount of butyrate in the test medium after culture)−(Amount of butyrate in a PYA medium without each indigestible saccharide after culture)

(Ratio of butyrate)=(Amount of butyrate in the test medium after culture)/((Amount of acetate+ Amount of propionate+Amount of butyrate) in the test medium after culture)×100   (Expression 3)

The results are shown in FIGS. 3 and 4. From FIGS. 3 and 4, YIT 12354 and YIT 12355 were found to be able to utilize indigestible saccharides more than the type strain YIT 10092$^T$ does, and also to have a larger amount of butyrate produced. The amounts of butyrate produced by the two isolates in the presence of L-sorbose both exhibited at least 1.5 times that of the type strain. The ratio of butyrate to total short-chain fatty acids was also found to be higher than that of the type strain YIT 10092$^T$.

Example 4

Butyrate Produced by Addition of Each Indigestible Saccharide and YIT 12355 into Mouse Feces, and Ratio of Butyrate to Total Short-chain Fatty Acids 0.8 g of mouse feces was diluted 12.5-fold with PBS, and 0.5% of each indigestible saccharide (lactitol, maltitol, D-mannitol, D-sorbitol, L-sorbose or D-xylitol) and 1.0% of YIT 12355 precultured in a PYGA medium were added thereto, followed by anaerobic culture at 37° C. for 24 hours. Also, a medium without each indigestible saccharide was also cultured in the same way as above. After the completion of the culture, the organic acid concentration in the culture solution was analyzed by ion-exclusion HPLC. The analysis conditions were the same as those described above in Example 2. After the quantification of the organic acid concentration, the amount of butyrate produced and the ratio of butyrate were calculated according to the same expression as (Expression 3).

The results are shown in FIGS. 5 and 6. As shown in FIGS. 5 and 6, butyrate production was largely increased by the addition of the combination of the butyrate-producing bacterium of the present invention and the indigestible saccharide, as compared with the case of the addition of the indigestible saccharide alone and the case of the addition of the butyrate-producing bacterium of the present invention alone. The ratio of butyrate to total short-chain fatty acids was also largely increased by the addition of the combination of the butyrate-producing bacterium of the present invention and the indigestible saccharide, as compared with the case of the addition of the indigestible saccharide alone and the case of the addition of the butyrate-producing bacterium of the present invention alone.

Example 5

Multiple Oral Dose Test of YIT 12355 to Mouse Given Indigestible Saccharide

1) Test Design

The overall test schedule is shown in Table 6. Mice were acclimatized and raised with F2 feed (manufactured by Funabashi Farm Co., Ltd.) for 1 week and then divided into 6 groups such that the average body weight was almost equal among these groups. Then, a control diet (Table 7) was administered thereto for 1 week and replaced with purified feed containing an indigestible material, which was then administered thereto for 2 weeks. A live cell suspension of YIT 12355 was orally administered twice a week a total of 4 times using a probe. At the final day of the test, each mouse was dissected, and the cecal and colonic contents were recovered and examined for an organic acid concentration. Also, the cell count of YIT 12355 in the intestinal tract contents was measured by quantitative PCR, while change in the whole intestinal flora was examined by use of PCR-DGGE (denaturing gradient gel electrophoresis).

<Test System>

Animal used: mouse C57BL/6J (4 weeks old; CLEA Japan, Inc.)

Test period: 3 weeks

Indigestible saccharide used: lactitol and maltitol

Dose of indigestible saccharide: 5% (w/w)

Administered bacterial strain: YIT 12355

Dose of bacterium: live cell dose: 3.9 to 6.9×10$^8$ cfu/mouse (administration of a suspension in physiological saline using a probe). Total cell count including dead cells: 3.6 to 4.6×10$^8$ cfu/mouse Group configuration: 6 groups (5 mice/group)

−/− group, Control

AH/− group, Administration of YIT 12355 alone

−/LAC group, Administration of lactitol alone

−/MAL group, Administration of maltitol alone

AH/LAC group, Administration of YIT 12355 and lactitol in combination

AH/MAL group, Administration of YIT 12355 and maltitol in combination

Feed composition: purified feed based on AIN-93G (Table 7)

Measurement item: cecal flora analysis (cell count measurement of the administered bacterium by quantitative PCR, total cell count measurement by the DAPI counting method, and observation of change in flora by PCR-DGGE)

TABLE 6

Test schedule

|  |  | Live cell or physiological saline administration (twice/week) ↓ ↓ ↓ ↓ |
|---|---|---|
| —/— group (control group) | Control diet (1 wk) | Control diet (2 wk) |
| AH/— group (AH group) | Control diet (1 wk) | Control diet (2 wk) |
| —/LAC group (LAC group) | Control diet (1 wk) | LAC-containing diet (2 wk) |
| —/MAL group (MAL group) | Control diet (1 wk) | MAL-containing diet (2 wk) |
| AH/LAC group | Control diet (1 wk) | LAC-containing diet (2 wk) |
| AH/MAL group | Control diet (1 wk) | LAC-containing diet (2 wk) ↓ Dissection |

TABLE 7

Feed composition

| | Content (%) | | |
|---|---|---|---|
| Composition | Control group AH group | LAC group AH/LAC group | MAL group AH/MAL group |
| α-Corn starch | 39.7486 | 34.7486 | 34.7486 |
| Vitamin-free casein | 20.00 | 20.00 | 20.00 |
| Dextrin | 13.20 | 13.20 | 13.20 |
| Sucrose | 10.00 | 10.00 | 10.00 |
| Soybean oil | 7.00 | 7.00 | 7.00 |
| Cellulose | 5.00 | 5.00 | 5.00 |
| Lactitol | — | 5.00 | — |
| Maltitol | — | — | 5.00 |
| AIN93G salt mix | 3.50 | 3.50 | 3.50 |
| AIN93G vitamin mix | 1.00 | 1.00 | 1.00 |
| L-Cystine | 0.300 | 0.300 | 0.300 |
| Choline tartrate | 0.25 | 0.25 | 0.25 |
| t-Butylhydroxytoluene | 0.0014 | 0.0014 | 0.0014 |
| Total | 100 | 100 | 100 |

2) Preparation and Cell Count Measurement of Administered Bacterium (YIT 12355)

YIT 12355 was cultured at 37° C. for 24 hours in a PYGA medium, and then centrifugation pellets were suspended in a 10% skim milk-2% sodium glutamate solution. The suspension was frozen at −80° C. to prepare a frozen stock. A bacterial solution of YIT 12355 for administration was prepared as follows using the frozen stock.

The frozen stock solution of YIT 12355 was thawed, and the solution was inoculated at 1% to 4 mL of a PYGA medium, followed by anaerobic culture at 37° C. for 24 hours. The culture solution was inoculated at 1% to 56 mL of a medium having the same composition as above, followed by anaerobic culture at 37° C. for 24 hours. The bacterial solution was centrifuged at 10,000 rpm at 4° C. for 10 minutes, and then the supernatant was removed. The pellets were resuspended by the addition of 30 mL of cold physiological saline anaerobically substituted in advance, and the supernatant was removed by centrifugation. The pellets were resuspended in 6 mL of cold physiological saline to prepare a bacterial solution for administration. The suspension of the bacterial cells was carried out in a glove box.

The bacterial solution was serially diluted with anaerobically substituted physiological saline and spread over a PYGA plate medium, followed by anaerobic culture at 37° C. for 24 hours. Then, colonies were counted, and a viable count was calculated. After fixation of a portion of the bacterial solution in a 4% solution of paraformaldehyde in PBS, the total cell count was measured by the DAPI counting method.

3) Collection of Intestinal Tract Contents

At the 2nd week of administration of the test feed, each mouse was anesthetized with diethyl ether and euthanized by cervical dislocation. After abdominal section, cecal tissues and colonic tissues were excised to recover their contents. The cecal and colonic contents were diluted 10-fold with PBS and subjected to DNA extraction.

4) Analysis of Flora in Intestinal Tract Contents a) Cell Count Measurement of YIT 12355 by Quantitative PCR DNA was extracted by the bead-phenol method from the 10-fold diluted solution of the intestinal tract contents. Specifically, 0.3 g of glass beads (diameter: 0.1 mm), 300 μL of a Tris-SDS solution (a mixed solution of 250 mL of 200 mM Tris-HCl, 80 mM EDTA, pH 9.0, and 50 mL of 10% SDS) and 500 μL of TE saturated phenol were added to 200 μL of the diluted solution of the intestinal tract contents, and the mixture was vigorously shaken for 30 seconds using FASTPREP FP120 cell disruptive equipment (power level: 5.0). After centrifugation at 15,000 rpm for 5 minutes, 400 μL of a phenol/chloroform/isoamyl alcohol (25:24:1) solution was added to 400 μL of the supernatant, and the mixture was shaken for 45 seconds using FASTPREP FP120 cell disruptive equipment (power level: 4.0). After centrifugation at 15,000 rpm for 5 minutes, 25 μL of 3 M sodium acetate (pH 5.4) and 250 μL of isopropanol were added to 250 μL of the supernatant and mixed therewith. After centrifugation at 15,000 rpm for 5 minutes, the supernatant was removed, and 500 μL of 70% ethanol was added thereto, followed by centrifugation again at 15,000 rpm for 5 minutes. The supernatant was removed, and the pellets were dried and dissolved in 1.0 mL of a TE buffer. The obtained DNA solution was diluted 10-fold with purified water to prepare a template DNA solution. For quantitative PCR, 7500 Real-Time PCR System (manufactured by Life Technologies Corp.) was used. The total volume of the reaction solution was set to 20 μL, and SYBR Premix Ex Taq II (Takara Bio Inc.) containing 1.0 μM each of primers, and the template DNA solution were mixed and then subjected to quantitative PCR. The reaction conditions involved heating at 95° C. for 2 minutes, followed by 40 repetitive cycles each involving reactions at 95° C. for 20 seconds, 55° C. for 20 seconds and 72° C. for 50 seconds, and subsequent reaction at 72° C. for 3 minutes. For subsequent Tm value analysis, after reaction at 60° C. for 1 minute, the temperature was elevated at a temperature gradient of 0.2° C./sec to 95° C. during which the fluorescence of SYBR Green I was measured to measure the dissociation temperature (Tm) of the double strand of the amplification product. The sequences of *A. hadrus*-specific primers used in the quantitative PCR are shown in Table 8. The calibration curve for use in the quantification of *A. hadrus* was prepared using, as a template, DNA extracted from the bacterial cells of *A. hadrus* YIT12355 prepared at a given cell count.

TABLE 8

A. hadrus-specific primer used in quantitative PCR

| Target bacterial species | Primer | Sequence (5'→3') | Amplification product length (bp) |
|---|---|---|---|
| A.hadrus | s-Ahad-F | AGGGCTTAACTCTGGGAC (SEQ ID NO: 1) | 405 |
| | s-Ahad-R | GGTTAAGGACCGGTCAGAA (SEQ ID NO: 2) | | b) Measurement of Occupancy of YIT 12355 to Total Cell Count in Intestine

After fixation of a portion of the 10-fold diluted solution of the intestinal tract contents in a 4% solution of paraformaldehyde in PBS, the total cell count was measured by the DAPI counting method. The cell count of YIT 12355 was divided by the total cell count to calculate an occupancy (%).

(Occupancy of YIT 12355) (%)=(Cell count of YIT 12355/Total cell count)×100    (Expression 4)

c) Analysis of Flora in Cecal Contents by PCR-DGGE

The DNA extracted in the preceding paragraph 4)-a was pooled on a group basis, and the 16S rRNA gene fragment (containing V3 and V4 regions) of the bacterium was amplified by PCR using the DNA pool as a template and primers with a GC clamp (Table 9). The PCR conditions involved 5 μL of 10×Ex Taq Buffer, 1 μL of a BSA (20 mg/mL) solution, 2 μL of 2.5 mM dNTP, 1 μL of a 25 pmol/μL primer solution, 1.25 units of Ex Taq polymerase HS (Takara Bio Inc.) and 0.1 ng of the template DNA in 50 μL of the reaction solution. The temperature conditions involved 94° C. for 5 minutes, (94° C. for 20 seconds, 55° C. for 45 seconds and 72° C. for 1 minute)×30 cycles and 72° C. for 7 minutes. The amplification product was purified using QIAquick PCR Purification Kit (manufactured by Qiagen N.V.), and then the DNA was applied to a gel at 200 ng/well. An 8% acrylamide gel (8% acrylamide/bis (37:5:1), 1×TAE (pH 8.0), 0.1% TEMED, 0.1% ammonium persulfate) provided with a denaturant concentration gradient of 35 to 50% (here, 100% denaturant means a mixture of 7 M urea and 40% formamide) using Gradient Former (Bio-Rad Laboratories, Inc.) was used to perform electrophoresis at 60° C. at 130 V for 5 minutes and subsequent electrophoresis at 70 V for 16 hours. After the electrophoresis, the gel was stained with GelRed (Biotium), and the bands were confirmed and photographed under UV lamp. In order to identify a band derived from A. hadrus YIT 12355, PCR was performed using, as a template, DNA extracted from purely cultured bacterial cells of the bacterial strain, and the amplified product was used as an electrophoresis sample.

TABLE 9

Primer used in PCR-DGGE

| Primer | Sequence (5'→3') |
|---|---|
| GC-341F | GCclamp*-CCTACGGGAGGCAGCAG (SEQ ID NO: 3) |
| 800R | GGACTACCAGGGTATCTAAT (SEQ ID NO: 4) |

*GCclamp= CGCCCGCCGCGCCCCGCGCCCGTCCCGCCGCCCCCGCCCG (SEQ ID NO: 5)

The results of measuring the total cell count and the cell count of YIT 12355 in the intestine, and the occupancy of YIT 12355 are shown in Table 10. The results of analyzing flora in the cecal contents by PCR-DGGE are shown in FIG. 7.

TABLE 10

| | Cell count ($\log_{10}$ cells/g contents) | | | |
|---|---|---|---|---|
| Group | A. hadrus | Detected count | Total cell count | Occupancy (%) |
| Cecal contents | | | | |
| —/— group | 6.0 | (1/5) | 10.9 ± 0.1 | 0.001 |
| AH/— group | 7.0 ± 1.1 | (4/5) | 10.9 ± 0.1 | 0.1 ± 0.1 |
| —/LAC group | 7.2 | (1/5) | 11.1 ± 0.1 | 0.014 |
| —/MAL group | 6.1 | (1/5) | 11.0 ± 0.1 | 0.001 |
| AH/LAC group | 10.5 ± 0.4 | (5/5) | 11.1 ± 0.1 | 27.5 ± 19.0 |
| AH/MAL group | 10.6 ± 0.2 | (5/5) | 11.0 ± 0.1 | 45.2 ± 8.5 |
| Colonic contents | | | | |
| —/— group | ND | (0/5) | 10.9 ± 0.1 | 0.000 |
| AH/— group | 7.2 ± 1.1 | (4/5) | 11.0 ± 0.0 | 0.1 ± 0.1 |
| —/LAC group | ND | (0/5) | 11.1 ± 0.1 | 0.000 |
| —/MAL group | ND | (0/5) | 11.0 ± 0.1 | 0.000 |
| AH/LAC group | 10.4 ± 0.4 | (5/5) | 11.1 ± 0.1 | 23.4 ± 15.6 |
| AH/MAL group | 10.5 ± 0.4 | (5/5) | 11.0 ± 0.1 | 41.3 ± 22.1 |

ND: <lower quantification limit 6.0 $\log_{10}$ (cells/g contents)

Table 10 demonstrated that the administration of YIT 12355 alone or the indigestible saccharide alone largely changes neither the cell count nor the occupancy of A. hadrus in the intestine, whereas the administration of the butyrate-producing bacterium of the present invention and the indigestible saccharide in combination drastically increases the cell count and the occupancy of A. hadrus.

As seen from FIG. 7, the band derived from YIT 12355 (circled in FIG. 7) was increased in the AH/LAC group and the AH/MAL group. Therefore, it was confirmed that the administration of the butyrate-producing bacterium of the present invention and the indigestible saccharide in combination specifically increased the butyrate-producing bacterium of the present invention even when change in the whole intestinal flora was observed.

Example 6

Single Oral Dose Test of YIT 12355 to Mouse Given Indigestible Saccharide

1) Test Design

The group configuration and the test schedule are shown in Table 11. Mice were acclimatized and raised with F2 feed for 1 week and then divided into 4 groups such that the average body weight was almost equal among these groups. A control diet (Table 12) was administered thereto for 1 week. Then, the control diet was administered to the control group (−/− group) and the AH/− group for 2 weeks while purified feed containing maltitol (MAL-containing diet) was administered to the −/MAL group and the AH/MAL group for 2 weeks. A live cell suspension of YIT 12355 was administered at a single dose using a probe after the administration of the control diet for 1 week. At the final day of the test, each mouse was dissected, and the cecal contents were recovered. The cecal contents were subjected to the cell count measurement of YIT 12355.

<Test System>
Test material: Maltitol (5% mixed feed administration)
Administered bacterial strain: YIT 12355
Animal species: Mouse C57BL/6J (4 weeks old; CLEA Japan, Inc.)
Group configuration: 7 mice×4 groups
  −/− group, Control
  AH/− group, Administration of YIT 12355 alone
  −/MAL group, Administration of maltitol alone
  AH/MAL group, Administration of YIT 12355 and maltitol in combination (see Table 11)
Test period: 3 weeks (1-week control diet+2-week MAL-containing diet or control diet)
Bacterium administration method: Single dose of a suspension of live cells in physiological saline using a probe
Feed composition: Purified solid feed based on AIN-93G (Table 12)
Test item: Cecal flora (cell count and occupancy of the administered bacterium)

TABLE 11

Test schedule

| | | Live cell or physiological saline administration (single dose) ↓ |
|---|---|---|
| −/− group | Control diet (1 wk) | Control diet (2 wk) |
| AH/− group | Control diet (1 wk) | Control diet (2 wk) |
| −/MAL group | Control diet (1 wk) | MAL-containing diet (2 wk) |
| AH/MAL group | Control diet (1 wk) | MAL-containing diet (2 wk) ↓ Dissection |

TABLE 12

Feed composition

| | Content (%) | |
|---|---|---|
| Composition | Control diet | MAL-containing diet |
| α-Corn starch | 39.7486 | 34.7486 |
| Vitamin-free casein | 20.00 | 20.00 |
| Dextrin | 13.20 | 13.20 |
| Sucrose | 10.00 | 10.00 |
| Soybean oil | 7.00 | 7.00 |
| Cellulose | 5.00 | 5.00 |
| Maltitol | — | 5.00 |
| AIN93G salt mix | 3.50 | 3.50 |
| AIN93G vitamin mix | 1.00 | 1.00 |
| L-Cystine | 0.300 | 0.300 |
| Choline tartrate | 0.25 | 0.25 |
| BHT | 0.0014 | 0.0014 |
| Total | 100 | 100 |

2) Preparation and Cell Count Measurement of Administered Bacterium (YIT 12355)

A live cell suspension of YIT 12355 (administered bacterium) was prepared in the same way as in the paragraph 2) of Example 5.

3) Administration of YIT 12355

The bacterial solution (viable count: $3.1 \times 10^9$ cfu/mL, total cell count: $1.9 \times 10^{10}$ cells/mL) prepared in the preceding paragraph 2) was orally administered at a single dose of 0.2 mL (viable count: $6.2 \times 10^8$ cfu/mouse, total cell count: $3.8 \times 10^9$ cells/mouse) to each mouse using a probe. To the control group and the −/MAL group, 0.2 mL of physiological saline was administered instead of the bacterial solution.

4) Sampling

At the 3rd week after the start of the test (at the 2nd week of administration of the bacterial solution using a probe), abdominal section was performed under Somnopentyl anesthesia, and each mouse was euthanized by the collection of the whole blood from the inferior vena cava. Then, the cecal contents were recovered. The cecal contents were diluted 10-fold with PBS and subjected to DNA extraction.

5) Cell Count Measurement of YIT 12355 in Cecal Contents

5)-1 Cell Count Measurement of YIT 12355 by Quantitative PCR

DNA was extracted by the bead-phenol method described in the paragraph 4)a) of Example 5 from the 10-fold diluted solution of the intestinal tract contents. The cell count of YIT 12355 was measured by quantitative PCR using the obtained DNA as a template and the bacterial species-specific primers described in the paragraph 4)a) of Example 5.

5)-2 Measurement of Occupancy of YIT 12355 to Total Cell Count in Intestine

After fixation of a portion of the 10-fold diluted solution of the intestinal tract contents in a 4% solution of paraformaldehyde in PBS, the total cell count was measured by the DAPI counting method. The cell count of YIT 12355 was divided by the total cell count to calculate an occupancy (%).

(Occupancy of YIT 12355) (%)=(Cell count of YIT 12355/Total cell count)×100   (Expression 5)

The results of measuring the total cell count in the intestine and the cell count of YIT 12355 and the occupancy of YIT 12355 are shown in Table 13. As seen from Table 13, the single dose of AH alone or the indigestible saccharide alone largely changes neither the cell count nor the occupancy, whereas the single dose of the butyrate-producing bacterium of the present invention and the indigestible saccharide in combination drastically increases the cell count and the occupancy, as with the case of the multiple administration.

TABLE 13

Cell count of *A. hadrus* YIT 12355 in cecum and ratio thereof to total cell count

| | Cell count log$_{10}$ (cells/g contents) | | |
|---|---|---|---|
| Group | *A. hadrus* YIT 12355 | Total cell count | Occupancy (%) |
| —/— group | <6.0 | 10.9 ± 0.3 | 0.0 |
| AH/— group | 8.0 ± 0.3 | 10.9 ± 0.4 | 0.3 |
| —/MAL group | <6.0 | 10.9 ± 0.1 | 0.0 |
| AH/MAL group | 10.1 ± 0.2 | 10.8 ± 0.3 | 21.3 ± 14.6 |

Example 7

Test on Relationship Between Increase in Cell Count of YIT 12355 and Butyrate Concentration 0.8 g of mouse fresh feces obtained 1 week after the start of the single dose test of Example 6 was collected into a sample tube and the tube was transferred into a glove box with the low-temperature and anaerobic state maintained. The feces were diluted with PBS anaerobically substituted in advance (final dilution: 12.5-fold), and a maltitol solution (final concentration: 0.5%) and/or a cultured bacterial solution of YIT 12355 (1% inoculated) was added thereto, followed by anaerobic culture at 37° C. for 24 hours. After the culture, the butyrate concentration was measured by ion-exclusion HPLC using an electric conductivity detector.

The results are shown in FIG. 8. Combined use of the butyrate-producing bacterium of the present invention and the indigestible saccharide in vitro increases the butyrate concentration with increase in cell count.

As seen from the results of Examples 5 to 7, the addition of the indigestible saccharide alone resulted in a cell count of YIT 12355 less than $10^6$ cells/mL, and did not increase the butyrate concentration. On the other hand, the addition of YIT 12355 alone increased the cell count of *A. hadrus* and accordingly increased the butyrate concentration. The combination of the indigestible saccharide and YIT 12355 increased the cell count of *A. hadrus* about 100 times that in the case of the addition of YIT 12355 alone and increased the butyrate concentration with the increase in cell count. This demonstrated that combined use of the butyrate-producing bacterium of the present invention and an indigestible saccharide increases a butyrate concentration with increase in cell count.

The invention claimed is:

1. A composition for a food or drink product, medicament or feed, the composition comprising
an indigestible saccharide and
a butyrate-producing bacterium belonging to *Anaerostipes hadrus* (*Eubacterium hadrum*), wherein
an amount of butyrate produced is at least 1.5 times that of *Anaerostipes hadrus* (*Eubacterium hadrum*) YIT $10092^T$ (DSM $3319^T$), and
the amount of butyrate produced is measured by a method comprising
thawing a frozen stock solution of a bacterial strain, in which bacterial cells are suspended at a cell count of 2.0 to $5.5 \times 10^{10}$ cells/mL in a 10% (w/v) skim milk-2% sodium glutamate solution,
inoculating the solution at 1% to 4 mL of a PYGA medium, which is a PY liquid medium supplemented with 33 mM sodium acetate and 0.5 (w/v) % glucose and culturing anaerobically at 37° C. for 24 hours to obtain a first culture solution,
then inoculating the first culture solution at 1% to a PYGA medium and culturing anaerobically at 37° C. for 24 hours to obtain a second culture solution,
then inoculating the second culture solution at 1% to a PY medium containing 33 mM sodium acetate and 0.5 (w/v) % L-sorbose and culturing anaerobically at 37° C. for 24 hours to obtain a third culture solution, and
then measuring the amount of butyrate in the third culture solution.

2. The composition according to claim 1, wherein the indigestible saccharide is one or more members selected from the group consisting of isomalt, isomaltulose, D-galactitol, D-xylitol, D-sorbitol, L-sorbose, maltitol, D-mannitol, lactitol and galactooligosaccharide.

3. The composition according to claim 1, wherein the butyrate-producing bacterium is *Anaerostipes hadrus* (*Eubacterium hadrum*) YIT 12354 (NITE BP-01831) or *Anaerostipes hadrus* (*Eubacterium hadrum*) YIT 12355 (NITE BP-01832).

4. The composition according to claim 3, wherein the indigestible saccharide is one or more members selected from the group consisting of isomalt,
isomaltulose, D-galactitol, D-xylitol, D-sorbitol, L-sorbose, maltitol, D-mannitol, lactitol and galactooligosaccharide.

* * * * *

SEQUENCE LISTING

```
<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Designed primer based on Anaerostipes hadrus
      gene

<400> SEQUENCE: 1
agggcttaac tctgggac                                                 18

<210> SEQ ID NO 2
<211> LENGTH: 19
<212> TYPE: DNA
<213> ORGANISM: Artificial Sequence
<220> FEATURE:
<223> OTHER INFORMATION: Designed primer based on Anaerostipes hadrus
      gene

<400> SEQUENCE: 2
ggttaaggac cggtcagaa                                                19

<210> SEQ ID NO 3
<211> LENGTH: 17
<212> TYPE: DNA
<213> ORGANISM: Artificial Sequence
<220> FEATURE:
<223> OTHER INFORMATION: Designed primer based on bacterial 16S rRNA
      gene

<400> SEQUENCE: 3
cctacgggag gcagcag                                                  17

<210> SEQ ID NO 4
<211> LENGTH: 20
<212> TYPE: DNA
<213> ORGANISM: Artificial Sequence
<220> FEATURE:
<223> OTHER INFORMATION: Designed primer based on bacterial 16S rRNA
      gene

<400> SEQUENCE: 4
ggactaccag ggtatctaat                                               20

<210> SEQ ID NO 5
<211> LENGTH: 40
<212> TYPE: DNA
<213> ORGANISM: Artificial Sequence
<220> FEATURE:
<223> OTHER INFORMATION: Designed primer for DGGE

<400> SEQUENCE: 5
cgcccgccgc gccccgcgcc cgtcccgccg ccccccgcccg                         40
```